(12) United States Patent
Verma

(10) Patent No.: US 9,960,415 B2
(45) Date of Patent: May 1, 2018

(54) CONDENSED SILICON-CARBON COMPOSITE

(71) Applicant: Robert Bosch GmbH, Stuttgart (DE)

(72) Inventor: Pallavi Verma, Leinfelden (DE)

(73) Assignee: ROBERT BOSCH GMBH, Stuttgart (DE)

( * ) Notice: Subject to any disclaimer, the term of this patent is extended or adjusted under 35 U.S.C. 154(b) by 0 days. days.

(21) Appl. No.: 15/115,388

(22) PCT Filed: Jan. 5, 2015

(86) PCT No.: PCT/EP2015/050051
§ 371 (c)(1),
(2) Date: Jul. 29, 2016

(87) PCT Pub. No.: WO2015/113781
PCT Pub. Date: Aug. 6, 2015

(65) Prior Publication Data
US 2017/0012278 A1    Jan. 12, 2017

(30) Foreign Application Priority Data

Jan. 30, 2014   (DE) .................. 10 2014 201 627

(51) Int. Cl.
| | |
|---|---|
| *C07F 7/04* | (2006.01) |
| *H01M 4/36* | (2006.01) |
| *H01M 4/134* | (2010.01) |
| *H01M 4/38* | (2006.01) |
| *H01M 4/587* | (2010.01) |
| *H01M 4/62* | (2006.01) |
| *C07F 7/02* | (2006.01) |
| *H01M 10/0525* | (2010.01) |
| *H01M 10/052* | (2010.01) |

(52) U.S. Cl.
CPC ............. *H01M 4/364* (2013.01); *C07F 7/025* (2013.01); *H01M 4/134* (2013.01); *H01M 4/362* (2013.01); *H01M 4/366* (2013.01); *H01M 4/386* (2013.01); *H01M 4/587* (2013.01); *H01M 4/625* (2013.01); *H01M 10/0525* (2013.01); *H01M 10/052* (2013.01)

(58) Field of Classification Search
CPC ............................. H01M 4/00; H01M 10/052
USPC ....................................................... 556/442
IPC ...................... C07F 7/025; H01M 4/00,10/052
See application file for complete search history.

(56) References Cited

U.S. PATENT DOCUMENTS

| | | |
|---|---|---|
| 2010/0193731 A1 | 8/2010 | Lee et al. |
| 2012/0013051 A1 | 1/2012 | Mah et al. |
| 2012/0034522 A1 | 2/2012 | Sheem et al. |
| 2012/0107693 A1 | 5/2012 | Ishida et al. |

FOREIGN PATENT DOCUMENTS

| | | | |
|---|---|---|---|
| WO | 2005114708 | 12/2005 | |
| WO | WO 2005114708 A2 * | 12/2005 | ............. B82Y 10/00 |

OTHER PUBLICATIONS

Pallavi Verma et al. "Formation of artificial solid electrolyte interphase by grafting for improving Li-ion intercalation and preventing exfoliation of graphite." Carbon, Elsevier, Oxford, GB. Bd 50, Nr. 7, 4. Feb. 2012, pp. 2599-2614.
Ko H et al. "Combing and bending of carbon nanotube arrays with confined microfluidic flow on patterned surfaces." Journal of Physical Chemistry. B (Inline), American Chemical Society, Columbus, OH, US, Bd. 108, Mar. 13, 2004, pp. 4385-4393.
Flatt A K et al. "Fabrication of carbon nanotube-molecule-silicon junctions." Journal of the American Chemical Society, American Chemical Society, Bd. 127, Jun. 29, 2005, pp. 8918-8919.
Martin C et al. "Graphite-grafted silicon nanocomposite as a negative electrode for lithium-ion batteries," Dec. 11, 2009, Advanced Materials 20091211 Wiley-VCH Verlag Deu. vol. 21, NR. 46, pp. 4735-4741, XP002936277.
International Search Report dated Mar. 12, 2015 for International Application PCT/EP2015/050051, filed Jan. 5, 2015.

* cited by examiner

*Primary Examiner* — Rosalynd Keys
*Assistant Examiner* — Kofi Adzamli
(74) *Attorney, Agent, or Firm* — Norton Rose Fulbright US LLP; Gerard Messina

(57) ABSTRACT

A silicon-carbon composite. In order to improve the cycle stability of a lithium cell equipped therewith, the silicon-carbon composite is produced by a condensation reaction of silicon particles surface-modified with a first condensation-capable group and carbon particles surface-modified with a second condensation-capable group, the silicon particles being covalently bonded to the carbon particles via the condensation reaction product of the first condensation-capable group and the second condensation-capable group. In addition, a method for the production thereof and to an electrode, an electrode material, and a lithium cell is described.

15 Claims, 5 Drawing Sheets

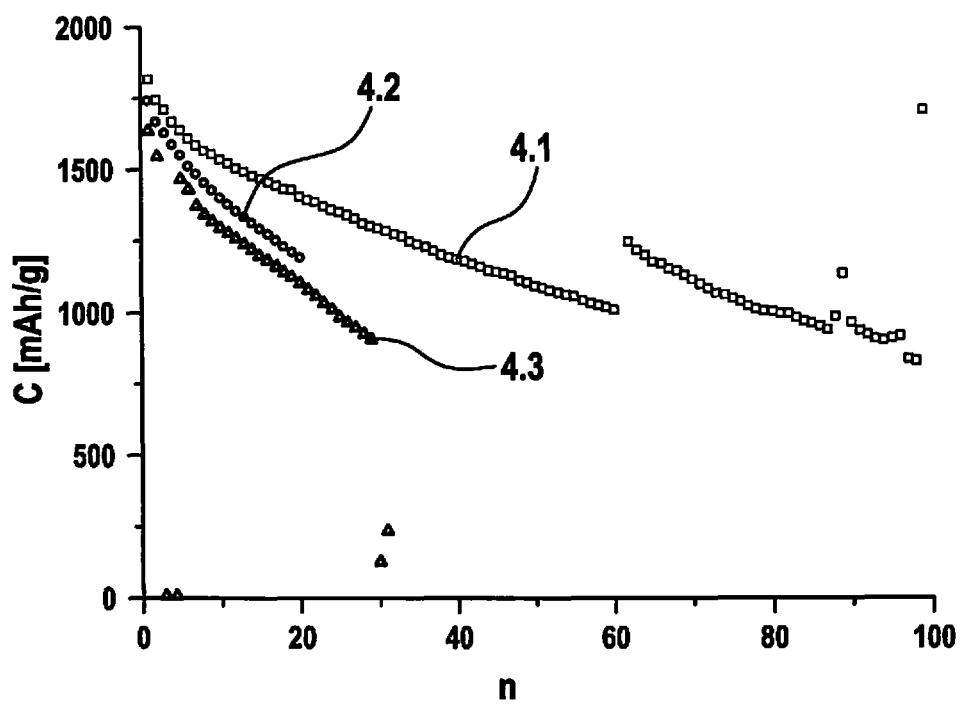

CONDENSED SILICON-CARBON COMPOSITE

FIELD

The present invention relates to a silicon-carbon composite, a method for its manufacture, as well as to an electrode, an electrode material, and a lithium cell containing same.

BACKGROUND INFORMATION

Silicon is a highly promising anode material for the next generation of lithium ion batteries, since it has a very high specific capacity of 4200 mAh/g (at 0.4 V against lithium), which is approximately eleven times higher than the specific capacity of graphite, which is 372 mAh/g. In addition, silicon is non-toxic and readily available.

However, presently silicon anodes still have a few limitations.

On the one hand, silicon has a low electrical conductivity; therefore, silicon anodes are ill suited for high-power applications.

On the other hand, silicon as an anode material in lithium ion batteries is subject to great volume fluctuations during the battery cycle. For example, lithium is embedded into silicon while the battery is charged, and forms an alloy, for example, according to the reaction Si+4.4 Li→Li$_{4.4}$Si, resulting inconsiderable expansion of the silicon volume. During discharge, lithium is released again, resulting in the silicon volume being considerably reduced again. As a result, when silicon particles are simply physically mixed with carbon particles, for example, for increasing the electrical conductivity, both particle-particle contacts and particle-current collector contacts are interrupted during the cycle, whereby the capacity of the silicon anode is considerably reduced during multiple cycles, which impairs cycle stability.

U.S. Patent Application Publication US 2010/0193731 A1 describes a composite anode material, which is manufactured with the aid of sintering and contains metal particles and carbon nanotubes covalently bonded to the metal particles.

U.S. Patent Application Publication US 2012/0107693 A1 describes an anode material for a lithium battery, which is manufactured with the aid of sputtering and includes a silicon-containing compound having the general formula SiC$_x$ with 0.05≤x≤1.5.

SUMMARY

The present invention relates to a silicon-carbon composite, which is manufactured by a condensation reaction, in particular, chemical condensation reaction, of silicon particles, which are surface-modified using a first condensation-capable group, and carbon particles, which are surface-modified using a second condensation-capable group.

The second condensation-capable group may be condensed with the first condensation-capable group, in particular, with the aid of a condensation reaction. Therefore, in particular, the first condensation-capable group may be referred to as first condensation-reaction-capable group, and the second condensation-capable group may be referred to as the second condensation-reaction-capable group.

In the condensation reaction, the first condensation-capable group may be covalently bonded to the second condensation-capable group, condensate being split off in particular.

Therefore, in particular, the silicon particles may be covalently bonded to the carbon particles via the condensation reaction product of the first condensation-capable group with the second condensation-capable group.

Covalent chemical bonds may be advantageously implemented between the silicon particles and the carbon particles via the condensation reaction. A chemically bonded silicon-carbon composite may thus be made advantageously available in a simple manner.

The chemically bonded silicon-carbon composite may be advantageously used as anode material or anode for lithium cells, for example, lithium ion cells, for example, in lithium ion batteries. The covalent chemical bonds between the silicon particles and the carbon particles make it possible to advantageously maintain a good contact between the silicon particles and the carbon particles during the cell cycles or battery cycles, and the related volume changes, for example, the volume expansion during charging and, in particular, during the repeated volume reduction during discharging. A stable silicon-carbon contact may thus be achieved, which remains stable during the cycle. In turn, the reduction in capacity may be counteracted, and improved cycle properties may be achieved.

Furthermore, a more stable electrical contact of the silicon particles with the electrically conductive carbon particles and of the composite with a current collector via the electrically conductive carbon particles may be achieved.

Overall, considerable improvement in the cycle stability may be achieved with the silicon-carbon composite both regarding a service life over numerous cycles and regarding a reduced capacity loss.

If necessary, the silicon-carbon composite may even withstand cycling at a 1 C rate. This and the good electrical connection make it advantageously possible to use the silicon-carbon composite even in high-power applications.

In addition, the covalent chemical bonds in the silicon-carbon composite may improve the mechanical stability of an electrode made thereof. In this case, the covalent chemical bonds may function as binders. This, in turn, makes it advantageously possible to reduce the proportion of, or possibly completely omit, the added binders. The specific energy density may thus be advantageously increased and/or the weight may be reduced.

The condensation reaction of the condensation-capable groups advantageously makes it possible to provide a silicon-carbon composite having these advantages in a simple and cost-effective manner. Highly stable silicon-carbon composite anodes may thus be advantageously provided for lithium cells, for example, lithium ion batteries in a simple and cost-effective manner.

In one specific embodiment, the condensation reaction is esterification, amidation, or peptide formation, etherification, polycondensation, nucleotide formation, or aldol condensation. For example, the condensation reaction may be esterification, amidation, peptide formation or etherification. For example, the condensation reaction may be esterification, amidation, or peptide formation. In particular, the condensation reaction may be esterification. The surface of silicon particles or carbon particles may be advantageously modified by these condensation reactions of condensation-capable groups in a simple manner.

In another specific embodiment, the first condensation-capable group is a hydroxyl group (—OH) or an amino group (—NH$_2$) or a carboxyl group (carboxylic acid group (—COOH). The second condensation-capable group may be a carboxyl group (carboxylic acid group (—COOH) or a hydroxyl group (—OH) or an amino group (—NH$_2$). A covalent chemical bond in the form of an ester unit (Si—O—C=O—C or Si—C=O—O—C) may be formed via esterification or a covalent chemical bond may be created in the form of an amide unit or a peptide unit (Si—NH—C=O—C or Si—C=O—NH—C) via amidation or peptide formation, respectively, or a covalent chemical bond in the form of an ether unit (Si—O—C) may be formed via etherification.

For example, the first condensation-capable group may be a hydroxyl group (—OH) or an amino group ($NH_2$), and the second condensation-capable group may be a carboxyl group (—COOH). For example, a covalent chemical bond in the form of an ester unit (Si—O—C=O—C) may be formed between the silicon particles and the carbon particles via esterification, or a covalent chemical bond in the form of an amide unit or peptide unit (Si—NH—C=O—C) may be formed via amidation or peptide formation, respectively. Conversely, however, the first condensation-capable group may also be a carboxyl group (—COOH) and the second condensation-capable group may be a hydroxyl group (—OH) or an amino group (—$NH_2$). For example, a covalent chemical bond in the form of an ester unit (Si—C=O—O—C) may be created between the silicon particles and carbon particles via esterification or a covalent chemical bond in the form of an amide unit or peptide unit (Si—C=O—NH—C) may be created via amidation or peptide formation, respectively.

In particular, the first condensation-capable group may be a hydroxyl group (—OH). Advantageously, hydroxyl groups may be easily formed on the surface of silicon particles in particular, for example, via treatment in an ultrasonic bath.

Therefore, in one embodiment, the first condensation-capable group is a hydroxyl group (—OH). The second condensation-capable group may be, for example, a carboxyl group (—COOH). Advantageously, carboxyl groups (—COOH) may be easily formed on the surface of carbon particles in particular, via a grafting reaction, for example.

A surface modification of silicon particles with the aid of hydroxyl groups (Si—OH) may be achieved, for example, via etching of silicon (Si) using a 5 mol % hydrogen fluoride solution and subsequent reaction with water vapor or liquid water in an ultrasonic bath (see *Chemical Reviews* (1995), Vol. 95, No. 5).

Therefore, in one embodiment, the surface modification of the silicon particles with the aid of a first functional group is achieved via etching of the silicon particles, for example, using hydrogen fluoride, for example, a 5 mol % hydrogen fluoride solution and subsequent hydrolysis, for example, by reacting with water vapor or liquid water, for example, in an ultrasonic bath.

Another option for surface modification of silicon particles with the aid of hydroxyl groups (Si—OH) includes grafting silicon (Si) using benzene-1,4-diol (see *Progress in Surface Science* (2003), 73, 1-56).

Therefore, in another embodiment, the surface modification of the silicon particles with the aid of the first functional group is produced via grafting silicon particles, for example, using a diol, for example, benzene-1,4-diol.

In the present invention it has been found that a surface modification of silicon particles with the aid of hydroxyl groups (Si—OH) may be achieved in a simple manner in particular, for example, according to the reaction equation: $SiO_2 + H_2O/H^+ \rightarrow SiOH$, via ultrasonic treatment, in an optionally acidified water bath.

Therefore, in a preferred embodiment, the surface modification of silicon particles with the aid of the first functional group is achieved by ultrasonic treatment of the silicon particles, in an optionally acidified water bath.

A surface modification of carbon particles with the aid of carboxyl groups (C—COOH), for example, may be achieved via non-aqueous in situ grafting, for example, using a para-carboxybenzene diazonium salt (see *Carbon* (2012), 50, 2599-2614).

Therefore, in another embodiment, the surface modification of the carbon particles with the aid of the second functional group is achieved via grafting, for example, via non-aqueous and/or in situ grafting of the carbon particles, for example, using a diazonium salt such as para-carboxybenzene diazonium salt.

The condensation-capable groups may be condensed, for example, with the aid of a condensation agent, for example, dicyclohexylcarbodiimide (DCC), a molecular sieve, and/or sulfuric acid ($H_2SO_4$).

In another specific embodiment, the carbon particles are graphite particles.

In another specific embodiment, the carbon particles have an average particle size ($d_{50}$), which is smaller than the average particle size ($d_{50}$) of the silicon particles. Advantageously, numerous contact points between carbon particles and silicon particles may thus be formed, whereby the electrical connection of the silicon particles may be further improved.

In another specific embodiment, the silicon particles have an average particle size ($d_{50}$) in a range of ≥200 nm to ≤100 µm. For example, the silicon particles may have an average particle size ($d_{50}$) in the range of ≥1 µm to ≤90 µm. In particular, the silicon particles may have an average particle size ($d_{50}$) in a range of ≥1 µm to ≤80 µm. This may have a favorable effect on the cycle stability, for example.

In another specific embodiment, the carbon particles, for example, graphite particles, have an average particle size ($d_{50}$) in a range of ≥1 µm to ≤50 µm. In particular, the carbon particles, for example, graphite particles, may have an average particle size ($d_{50}$) in a range of ≥10 µm to ≤25 µm. Good electrical connection to silicon particles may thus be advantageously achieved.

For example, the silicon particles and the carbon particles may have a molar ratio in a range between 1.5:1 and 1:1.5, for example, in a range between 1.2:1 and 1:1.2, for example, approximately 1:1. A maximum number of contact points between the silicon particles and the carbon particles may thus be advantageously achieved and, for example, the mechanical stability of the composite may thus be increased.

Regarding further technical features and advantages of the composite according to the present invention explicit reference is hereby made to the explanations in connection with the method according to the present invention, the electrode according to the present invention, the electrode material according to the present invention, and the cell and the battery according to the present invention, as well as to the figures and the description of the figures.

The present invention also relates to a method for manufacturing a silicon-carbon composite, for example, a silicon-carbon composite according to the present invention.

According to the present invention, for example, in a first method step a), silicon particles are provided with a surface modification involving a first condensation-capable group, and/or carbon particles are provided with a surface modification involving a second condensation-capable group. The second condensation-capable group may be capable of condensing with the first condensation-capable group in particular, and the first condensation-capable group and the second condensation-capable group may react with each other in a condensation reaction.

The silicon particles and the carbon particles may then react (with each other), for example, in a method step b) in a condensation reaction.

In one specific embodiment, the silicon particles are surface-modified by ultrasonic treatment in an optionally acidified water bath, for example, before or in method step a). Silicon oxide may be converted into silicon hydroxide, for example, in this process.

In a further specific embodiment, the carbon particles are surface-modified by grafting, for example, non-aqueous and/or in situ grafting, for example, of a diazonium salt such as para-carboxybenzene-diazonium salt before or in method step a).

In a further specific embodiment, the condensation reaction or method step b) takes place in the presence of a condensation agent. For example, dicyclohexylcarbodiimide (DCC), a molecular sieve, and/or sulfuric acid ($H_2SO_4$) may be used as condensation agents. In particular, the condensation agent may include or may be dicyclohexylcarbodiimide (DCC).

Regarding further technical features and advantages of the method according to the present invention explicit reference is hereby made to the explanations in connection with the composite according to the present invention, the electrode according to the present invention, the electrode material according to the present invention, and the cell and battery according to the present invention, as well as to the figures and the description of the figures.

Furthermore, the present invention relates to an electrode or an electrode material, which includes a silicon-carbon composite according to the present invention and/or a silicon-carbon composite manufactured according to the present invention. The electrode may be, for example, a silicon-carbon composite electrode, or the electrode material may be a silicon-carbon composite electrode material. For example, the electrode may be an anode, or the electrode material may be an anode material, for example, for a lithium cell, for example, a lithium ion cell, for example, a lithium ion battery.

Regarding further technical features and advantages of the electrode or the electrode material according to the present invention, explicit reference is hereby made to the explanations in connection with the composite according to the present invention, the method according to the present invention, and the cell and battery according to the present invention, as well as to the figures and the description of the figures.

The present invention further relates to a lithium cell or lithium battery, which includes a silicon-carbon composite according to the present invention and/or a silicon-carbon composite manufactured according to the present invention and/or an electrode according to the present invention and/or an electrode material according to the present invention. For example, the lithium cell may be a lithium ion cell, and the lithium battery may be a lithium ion battery.

Regarding further technical features and advantages of the cell or battery according to the present invention, explicit reference is hereby made to the explanations in connection with the composite according to the present invention, the method according to the present invention, and the electrode and electrode material according to the present invention, as well as to the figures and the description of the figures.

DETAILED DESCRIPTION OF EXAMPLE EMBODIMENTS

Further advantages and advantageous embodiments of the objects of the present invention are illustrated via the exemplary embodiments and drawings and further explained in the description that follows. It is important to keep in mind that the exemplary embodiments and figures have only descriptive character and are not intended to limit the present invention in any way.

Exemplary Embodiments

Example 1: Manufacture of with Surface-Modified Silicon Particles

Crystalline silicon particle powder having a particle size $d_{50}$ of 82 μm was subjected to ultrasonic treatment in distilled water for one hour. The powder was then filtered using a Whatman filter paper (No. 1821 150). The powder was dried at room temperature overnight.

The ultrasonically treated silicon particles were examined with the aid of X-ray photoelectron spectroscopy (XPS). The Si2p X-ray photoelectron spectrum of the treated silicon particles is depicted in FIG. 2b.

For comparison purposes, an X-ray photoelectron spectrum of the untreated silicon particles was also measured. The X-ray photoelectron spectrum of the untreated silicon particles is depicted in FIG. 2a.

Example 2: Manufacture of Carbon Particles Grafted Using Carboxyl Groups, in Particular, of Graphite Particles, Via Non-Aqueous Grafting 4.97 g p-aminobenzoic acid was agitated in 625 ml acetonitrile in the presence of air. 5 g graphite particles (SFG6L by Timcal, Switzerland) were added. Subsequently 9.25 ml tert-butyl nitrite was added dropwise under constant, vigorous agitation. The mixture was agitated for two hours. The resulting powder was filtered through a Büchner funnel equipped with a Whatman filter paper (No. 1442 126) and washed using acetonitrile. The powder was dried in a hood overnight and subsequently ground.

The carboxyl group-grafted graphite particles were examined with the aid of X-ray photoelectron spectroscopy (XPS). The C1s X-ray photoelectron spectrum of the carboxyl group-grafted graphite particles is depicted in FIG. 3b.

For comparison purposes, an X-ray photoelectron spectrum of the untreated graphite particles was also measured. The X-ray photoelectron spectrum of the untreated graphite particles is depicted in FIG. 3a.

Example 3: Manufacture of a Silicon-Carbon Composite Via Condensation Reaction of Carboxyl Group-Grafted Carbon Particles and Surface-Modified Silicon Particles 0.64 g of the surface-modified graphite particle powder from Example 2 was mixed in approximately 75 ml acetonitrile. Subsequently 1.5 g of the surface-modified silicon particle powder from Example 1 was added. The molar ratio of carbon powder to silicon powder was approximately 1:1. The mixture was heated to 45° C. under agitation. 21.0 ml dicyclohexylcarbodiimide (DCC) was liquefied using a water bath at a temperature above its melting point. The dicyclohexylcarbodiimide was then added to the mixture and agitated for another two hours at increased temperature. The container was then covered with Parafilm. After two hours, the heat input was interrupted and the mixture was agitated overnight at room temperature and then filtered with the aid of a filter paper. The powder was washed twice using acetonitrile and dried in a hood.

The condensation product of the ultrasonically treated silicon particles with the carboxyl group-grafted graphite particles was examined with the aid of X-ray photoelectron spectroscopy (XPS). The Si2p X-ray photoelectron spectrum is depicted in FIG. 2c and the C1s X-ray photoelectron spectrum is depicted in FIG. 3c.

Example 4: Half-Cell Tests

Multiple half-cells having the composition: 51 wt. % silicon, 22 wt. % graphite, 9 wt. % carboxymethylcellulose (CMC), 12 wt. % Super P, and 6 wt. % styrene-butadiene rubber (SBR) were produced.

In Example 4.1, which corresponds to a specific embodiment according to the present invention, silicon and graphite were used in the form of the silicon-carbon composite from Example 3.

In comparative Examples 4.2 and 4.3, silicon and graphite were used in the form of a physical mixture of crystalline silicon powder having an average particle size $d_{50}$ of 82 μm and graphite particles (SFG6L by Timcal, Switzerland).

The half-cells were tested using a half-cell BaSyTec instrument. The results of the half-cell tests are depicted in FIG. 4.

BRIEF DESCRIPTION OF THE DRAWINGS

FIG. 4 shows a graph for illustrating the variation of the specific capacity as a function of the number of cycles of one specific embodiment of a silicon-carbon composite according to the present invention and of simple physical mixtures of silicon particles and graphite particles.

DETAILED DESCRIPTION OF THE FIGURES SHOWING EXAMPLE EMBODIMENTS

Figure 1:
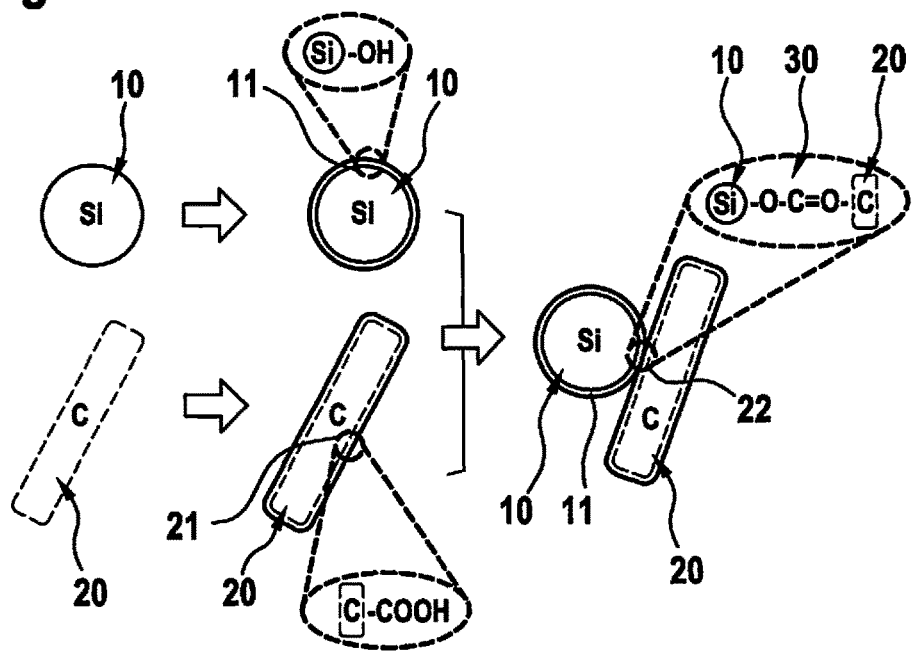
FIG. 1 shows a schematic representation illustrating a specific embodiment of a silicon-carbon composite according to the present invention manufactured using a condensation reaction.

FIG. 1 illustrates a specific embodiment of a silicon-carbon composite manufactured according to the present invention via a condensation reaction.

FIG. 1 shows that silicon particles 10 are subjected to a surface modification, in which condensation-capable hydroxyl groups 11 (—OH) are formed on the surface of silicon particles 10 (Si—OH).

FIG. 1 shows that carbon particles 20, for example, graphite particles, are subjected to a surface modification, in which condensation-capable carboxyl groups 21 (—COOH) are formed on the surface of carbon particles 20 (C—COOH).

FIG. 1 further shows that condensation-capable hydroxyl groups 11 of silicon particles 10 and condensation-capable carboxyl groups 21 of carbon particles 20 are subjected to a condensation reaction, in which covalent bonds in the form of ester groups (—O—C=O—) are formed between silicon particles 10 and carbon particles 20 (Si—O—C=O—C) via the condensation reaction.

Figure 2A:
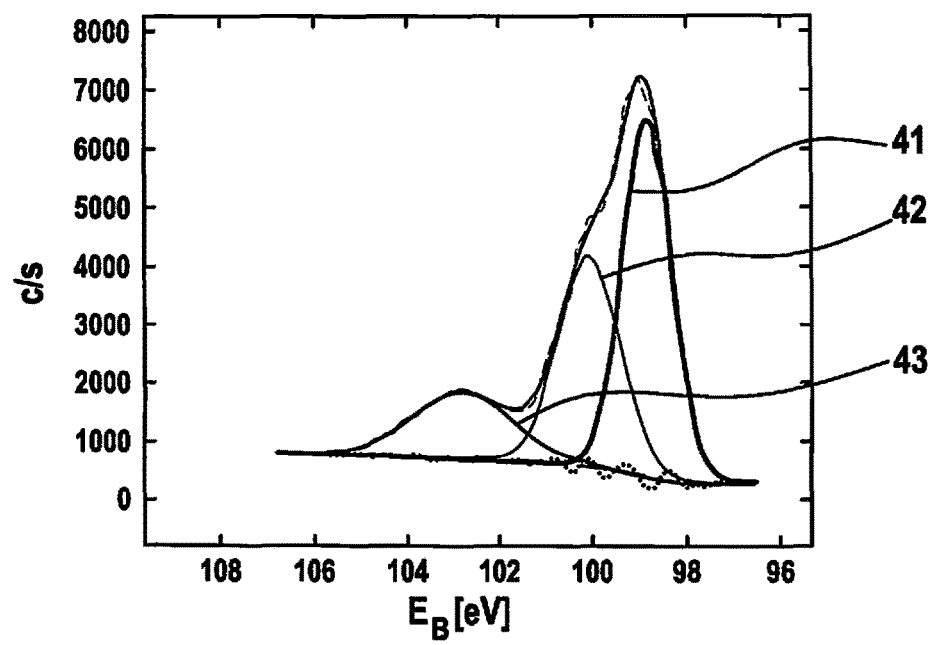
FIGS. 2a through 2c show Si2p XPS spectra for illustrating the surface modification and condensation reaction of the silicon particles.
Figure 2B:
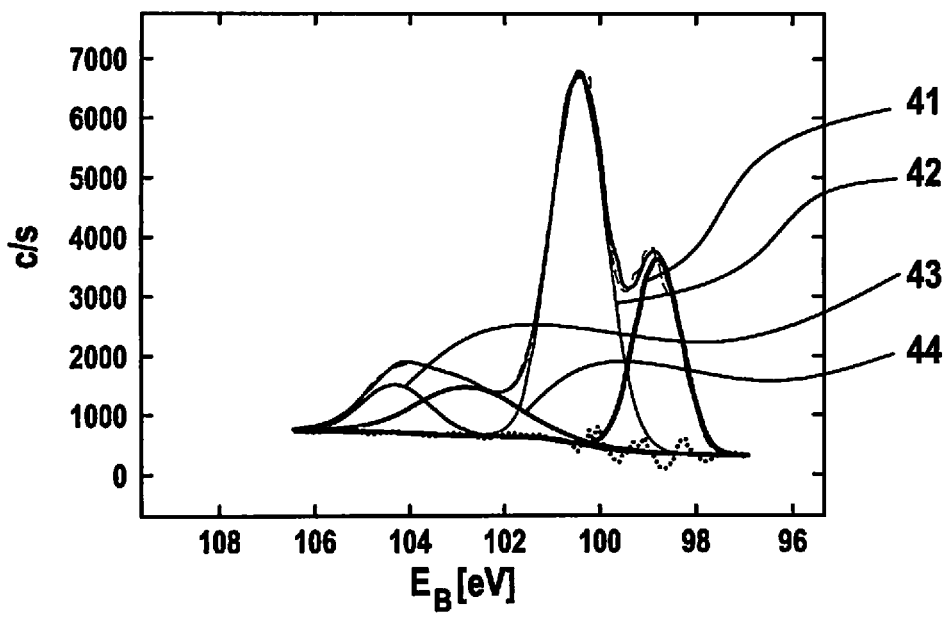
Figure 2C:
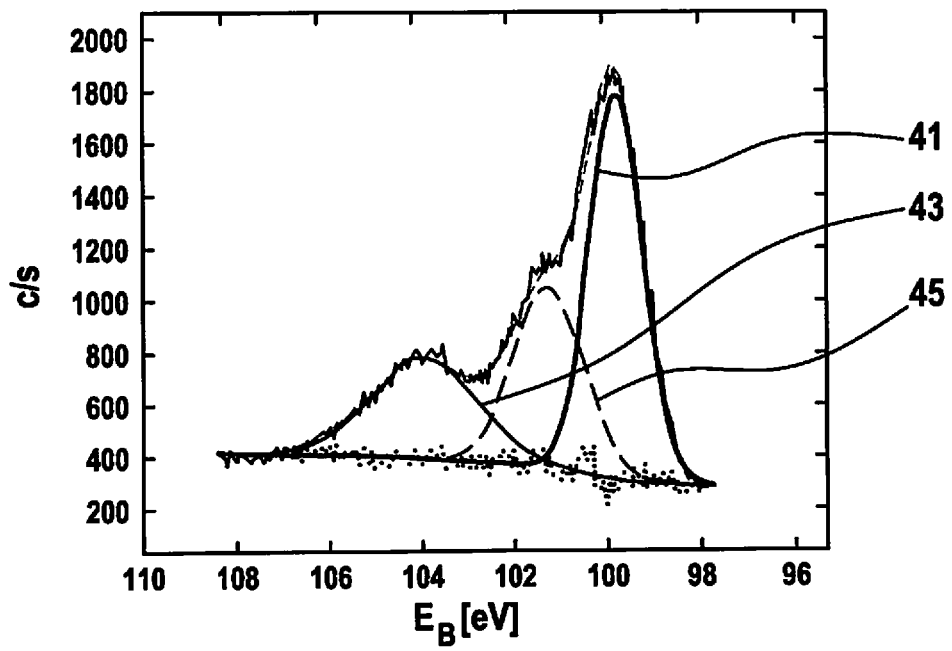

FIGS. 2a through 2c show Si2p X-ray photoelectron spectra (XPS spectra) for illustrating the surface modification and condensation reaction of the silicon particles.

Figure 3A:
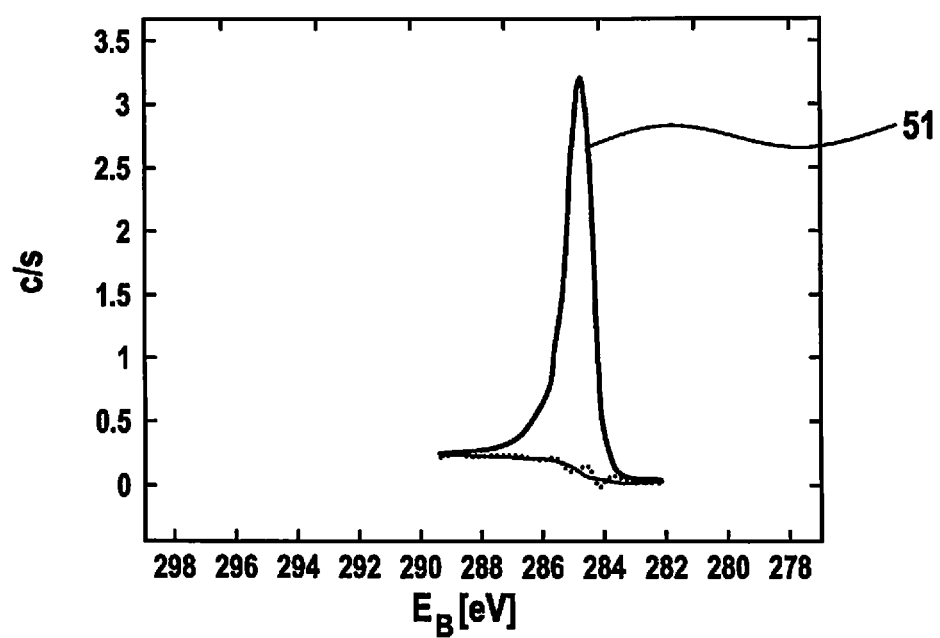
FIGS. 3a through 3c show C1s XPS spectra for illustrating the surface modification and condensation reaction of the carbon particles.
Figure 3B:
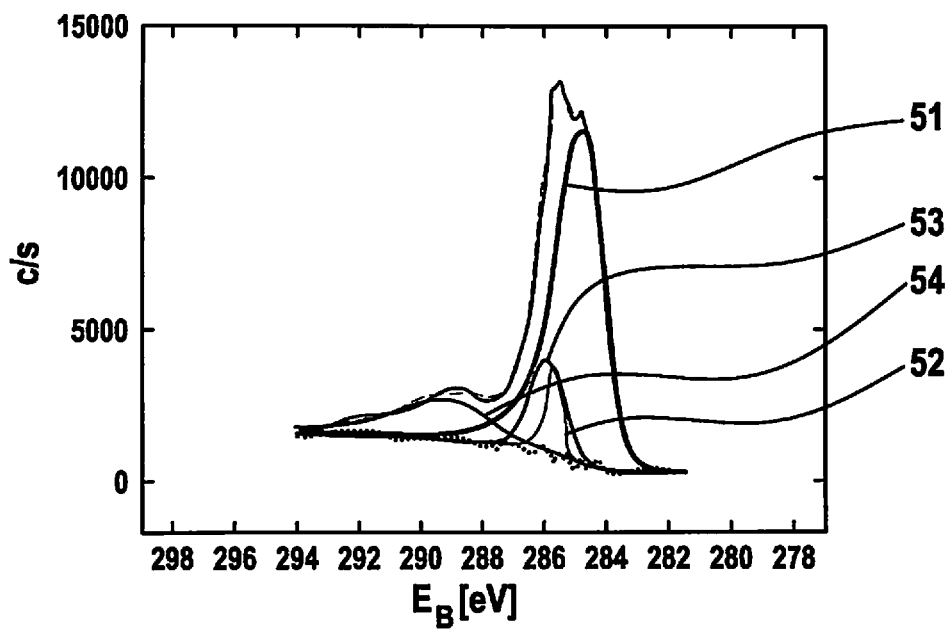
Figure 3C:
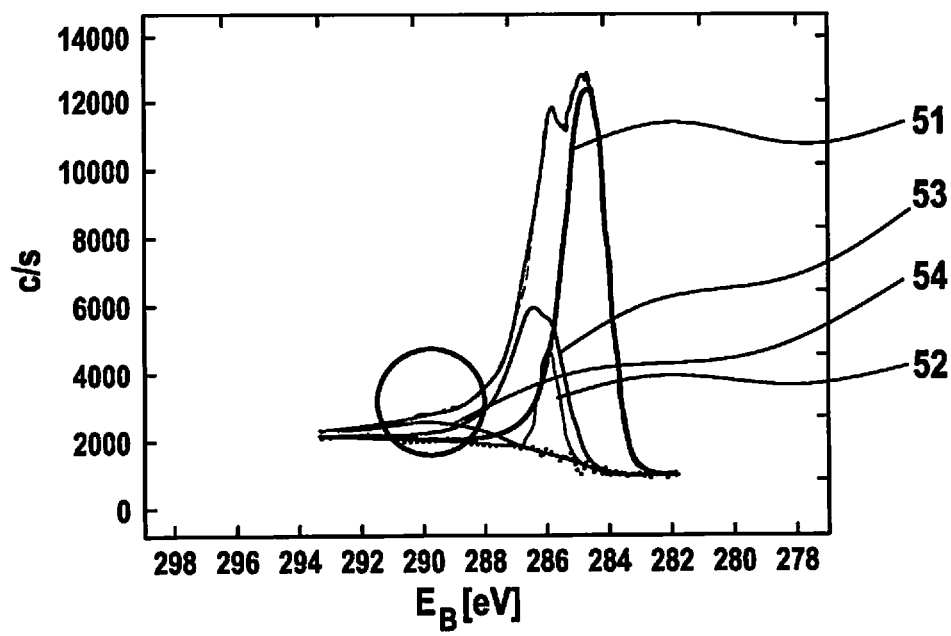

FIGS. 3a through 3c show C1s X-ray photoelectron spectra (XPS spectra) for illustrating the surface modification and condensation reaction of the carbon particles;

In FIGS. 2a through 2c and 3a through 3c, counts per second (C/s) are plotted against bond energy $E_B$ (eV). The relative quantities of different oxidation levels of silicon and carbon are ascertained and illustrated.

FIG. 2a shows a Si2p X-ray photoelectron spectrum of the original and untreated silicon particles used in Example 1 as source material, i.e., before the surface modification with the aid of ultrasonics, which have an average particle size $d_{50}$ of 82 μm. A peak identified by reference numeral 41 was ascertained for elemental silicon (Si bulk), a peak identified by reference numeral 42 was ascertained for $Si_2O$, and a peak identified by reference numeral 43 was ascertained for $SiO_2$.

FIG. 2b shows a Si2p X-ray photoelectron spectrum of the ultrasonically treated silicon particles (Si—OH) from Example 1, i.e., after the surface modification with the aid of an ultrasonic bath and before the condensation reaction. A peak identified by reference numeral 41 was ascertained for elemental silicon (Si bulk), a peak identified by reference numeral 42 was ascertained for $Si_2O$, a peak identified by reference numeral 43 was ascertained for $SiO_2$ and a peak identified by reference numeral 44 was ascertained for $Si_2O_3$.

A comparison of FIGS. 2a and 2b shows that the proportion of higher oxidation levels is obviously increased by the ultrasonic treatment. In particular, the 1+ or Si$^+$ oxidation level represented by $Si_2O$ 42 shows that OH bonds were formed on the surface of silicon (Si—OH) as a result of the ultrasonic treatment.

FIG. 3a shows a C1s X-ray photoelectron spectrum of the original and untreated graphite particles used in Example 2 as source material, i.e., before surface modification with the aid of grafting. A peak identified by reference numeral 51 was ascertained for elemental carbon (C—C). FIG. 3a shows that the untreated graphite particles are formed from elemental carbon.

FIG. 3b shows a C1s X-ray photoelectron spectrum of the carboxyl group-grafted graphite particles (graphite-COOH) from Example 2, i.e., after the surface modification with the aid of grafting and before the condensation reaction. A peak identified by reference numeral 51 was ascertained for elemental carbon (C—C), a peak identified by reference numeral 52 was ascertained for C—N=, a peak identified by reference numeral 53 was ascertained for C—O—C and a peak identified by reference numeral 54 was ascertained for O—C=O.

A comparison of FIGS. 3a and 3b shows that the proportion of the C—C bonds normally present in pure graphite has been clearly reduced by the chemical modification, and the proportion of carboxyl groups has clearly increased, which indicates a successful chemical modification of graphite by COOH— groups.

FIG. 2c shows a Si2p X-ray photoelectron spectrum of the product from Example 3, i.e., after the condensation reaction, which was produced by the condensation reaction of ultrasonically treated silicon particles from Example 1 with the carboxyl group-grafted graphite particles from Example 2. The peak identified by reference numeral 41 was ascertained for elemental silicon (Si bulk), the peak identified by reference numeral 43 was ascertained for $SiO_2$, and the peak identified by reference numeral 45 was ascertained for SiO.

FIG. 2c shows that the binding state of silicon has been subjected to a further significant change as a result of the condensation reaction. In particular, FIG. 2c shows that no more $Si^+$ (previously 42) is detected. The disappearance of the $Si^+$ peak (previously 42) and the related reduction in hydroxyl groups (OH— groups) may be explained by a successful reaction between dicyclohexylcarbodiimide (DCC) functioning as a water-removing condensation agent and the surface groups.

FIG. 3c shows a C1s X-ray photoelectron spectrum of the product from Example 3, i.e., after the condensation reaction, which was produced by the condensation reaction of the ultrasonically treated silicon particles from Example 1 with the carboxyl group-grafted graphite particles from Example 2. The peak identified by reference numeral 51 was ascertained for elemental carbon (C—C), the peak identified by reference numeral 52 was ascertained for C—N=, the peak identified by reference numeral 53 was ascertained for C—O—C, and the peak identified by reference numeral 54 was ascertained for O—C=O.

The portion of the spectrum circled in FIG. 3b shows that the proportion of carboxyl groups (—COOH) 54 is significantly reduced by the condensation reaction. This also demonstrates a successful reaction with dicyclohexylcarbodiimide (DCC) as dehydrating agent or water-removing condensation agent. In this reaction dicyclohexylcarbodiimide (DCC) is hydrated with the formation of dicyclohexylurea, which is soluble in organic solvents and may be removed by filtration.

The increase in oxygen bonds and simultaneous reduction in carboxyl groups proves a successful condensation reaction and surface modification by covalent bonds between the silicon and graphite particles.

FIG. 4 depicts the results of the half-cell tests from Example 4. In FIG. 4 the variation of specific capacity C [mA/h] as a function of cycle count n of the surface-modified condensed silicon-carbon composite from Example 4.1 is compared with the simple physical mixtures of silicon particles and graphite particles from Examples 4.2 and 4.3 as comparative examples.

The curve identified by reference numeral 4.1 depicts the results of a measurement at a C/10 rate of the surface-modified and condensed silicon-carbon composite from Example 4.1, which includes silicon particles having an average particle size $d_{50}$ of 82 μm.

The curve identified by reference numeral 4.2 depicts the results of a measurement at a C/10 rate of the simple physical mixture of silicon particles having an average particle size $d_{50}$ of 82 μm and graphite particles from Example 4.2, used as a comparative example.

The curve identified by reference numeral 4.3 depicts the results of a measurement at a C/20 rate of the simple physical mixture of silicon particles having an average particle size $d_{50}$ of 82 μm and graphite particles from Example 4.3, used as a comparative example.

The curves identified by reference numerals 4.2 and 4.3 show that both at a C/10 rate and even at a lower C/20 rate, using which normally higher capacities may be measured than at a C/10 rate, the comparative cells barely withstand 25 cycles.

The curve identified by reference numeral 4.1 shows that the surface-modified and condensed silicon-carbon composite according to the present invention from Example 4.1 has both a significantly better cycle stability, in particular, regarding a service life over multiple cycles and a lower capacity loss than both comparative examples 4.2 and 4.3, even at the higher C/10 rate. The jump in the 60 cycle count area is caused by an operating error of the BaSyTec instrument.

What is claimed is:

1. A method, comprising:
    forming a silicon-carbon composite by reacting, in a condensation reaction, silicon particles that are surface-modified with a first condensation-capable group and carbon particles that are surface-modified with a second condensation-capable group capable of condensing with the first condensation-capable group;
    wherein the silicon particles are covalently bonded to the carbon particles via a product of the condensation reaction in which the first condensation-capable group reacts with the second condensation-capable group.

2. The method as recited in claim 1, wherein the silicon particles are covalently bonded to the carbon particles via a product of the condensation reaction in which the first condensation-capable group reacts with the second condensation-capable group.

3. The method as recited in claim 1, wherein the condensation reaction is esterification, amidation, etherification, polycondensation, nucleotide formation, or aldol condensation.

4. The method as recited in claim 1, wherein the first condensation-capable group is a hydroxyl group, an amino group, or a carboxyl group, and the second condensation-capable group is a carboxyl group, a hydroxyl group, or an amino group.

5. The method as recited in claim 1, wherein the first condensation-capable group is a hydroxyl group and the second condensation-capable group is a carboxyl group.

6. The method as recited in claim 1, wherein the carbon particles have an average particle size which is smaller than an average particle size of the silicon particles.

7. The method as recited in claim 1, wherein the silicon particles have an average particle size in a range of ≥200 nm to ≤100 μm.

8. The method as recited in claim 1, wherein the carbon particles have an average particle size in a range of ≥1 μm to ≤50 μm.

9. The method as recited in claim 1, wherein the carbon particles are graphite particles.

10. The method as recited in claim 1, further comprising:
    surface-modifying the silicon particles with the first condensation-capable group by at least one of:
        i) ultrasonic treatment in an optionally acidified water bath,
        ii) etching using hydrogen fluoride, and hydrolyzing, and
        iii) grafting.

11. The method as recited in claim 1, further comprising:
    surface-modifying the carbon particles with the second condensation-capable group by grafting.

12. The method as recited in claim 1, wherein the reacting takes place in the presence of a condensation agent, the condensation agent being at least one of dicyclohexylcarbodiimide, a molecular sieve, and sulfuric acid.

13. The method as recited in claim 1, further comprising:
    arranging the silicon-carbon composite as an anode of a lithium cell or battery.

14. The method as recited in claim 1, further comprising:
    arranging the silicon-carbon composite as one of an electrode material and an anode material of a lithium cell or battery.

15. The method of claim 1, further comprising:
arranging the silicon-carbon composite in a lithium cell or battery as, or as part of, an electrode of the lithium cell or battery.

* * * * *